United States Patent
Szczech et al.

(10) Patent No.: US 7,351,205 B2
(45) Date of Patent: Apr. 1, 2008

(54) SHALLOW ANGLE NEEDLE GUIDE APPARATUS AND METHOD

(75) Inventors: Gerald S. Szczech, Coralville, IA (US); Craig Cermak, Riverside, IA (US); Brett Severence, Iowa City, IA (US)

(73) Assignee: CIVCO Medical Instruments Co., Inc., Kalona, IA (US)

( * ) Notice: Subject to any disclaimer, the term of this patent is extended or adjusted under 35 U.S.C. 154(b) by 0 days.

(21) Appl. No.: 10/336,098

(22) Filed: Jan. 3, 2003

(65) Prior Publication Data

US 2004/0133111 A1    Jul. 8, 2004

(51) Int. Cl.
*A61B 8/00* (2006.01)
(52) U.S. Cl. ..................................... 600/461
(58) Field of Classification Search ........ 600/407–471, 600/374, 573, 576, 581; 604/20–27; 606/159, 606/167; 73/625, 626; 607/22; 128/898, 128/916
See application file for complete search history.

(56) References Cited

U.S. PATENT DOCUMENTS

| | | | | |
|---|---|---|---|---|
| 4,497,325 A | * | 2/1985 | Wedel | 600/567 |
| 4,635,644 A | * | 1/1987 | Yagata | 600/464 |
| 4,911,173 A | * | 3/1990 | Terwilliger | 600/464 |
| 5,052,396 A | | 10/1991 | Wedel et al. | |
| 5,235,987 A | * | 8/1993 | Wolfe | 600/461 |
| 5,456,258 A | * | 10/1995 | Kondo et al. | 600/463 |
| 5,941,889 A | | 8/1999 | Cermak | |
| 6,149,598 A | * | 11/2000 | Tanaka | 600/462 |
| 6,245,028 B1 | * | 6/2001 | Furst et al. | 600/568 |
| 6,261,234 B1 | * | 7/2001 | Lin | 600/461 |
| 6,277,066 B1 | | 8/2001 | Irwin | |
| 6,296,614 B1 | | 10/2001 | Pruter | |
| 6,301,989 B1 | | 10/2001 | Brown et al. | |
| 6,361,499 B1 | | 3/2002 | Bates et al. | |
| 6,368,280 B1 | | 4/2002 | Cermak et al. | |
| 6,379,307 B1 | * | 4/2002 | Filly et al. | 600/461 |
| 6,916,328 B2 | * | 7/2005 | Brett | 606/167 |

* cited by examiner

*Primary Examiner*—Francis J. Jaworski
(74) *Attorney, Agent, or Firm*—Steptoe & Johnson LLP (57) ABSTRACT

A needle guide for use with an imaging instrument is disclosed. The needle guide is suitable for delivery of a needle at a shallow angle into a patient during imaging analysis. Thus, the needle guide is well suited to the controlled collection of biopsy tissue or other sample material near the surface of a patient.

53 Claims, 8 Drawing Sheets

SHALLOW ANGLE NEEDLE GUIDE APPARATUS AND METHOD

FIELD OF THE INVENTION

The present invention relates to a device for guiding a needle into a patient during imaging analysis. More particularly, the invention is directed to an apparatus for guiding a needle into a patient at a shallow angle such that the needle can strike targets near the surface of the patient.

BACKGROUND

Imaging instruments, such as ultrasound probes, have revolutionized the manner in which many important medical procedures are performed. These medical instruments utilize substantially non-invasive imaging techniques to explore and assess the condition of human tissue. As a result of these non-invasive imaging techniques, diagnostic and therapeutic protocols have been developed that allow many highly successful and safe procedures to be performed with a minimum of disturbance to patients.

Ultrasound and other imaging techniques have received widespread acceptance as useful diagnostic tools. An ultrasound image, for example, is created by emission of very high frequency sound waves from a transducer scanning the subject area. The sound waves are reflected back to the transducer, and corresponding data is transmitted to a processing device. The processing device analyzes the data and composes a picture for display on a monitoring screen. Ultrasound probes, and other imaging instruments, may be used in this manner for a variety of purposes, such as identifying the existence, location, and size of tumors, as well as the existence of other medical conditions, including the atrophy or hypertrophy of bodily organs.

It is often desirable to use imaging techniques to guide a needle into a patient. For example, needles can be guided into a tumor to collect a biopsy sample, or can be guided into a location to administer a therapeutic agent. Unfortunately, one significant challenge associated with imaging analysis is that it can be difficult to precisely direct a needle to a target identified during the imaging analysis. Fortunately, a number of quality needle guides have been developed to help direct a needle into a patient. Although these needle guides are useful, they generally do not allow for the precise placement of a needle at shallow angles into targets near the surface of the patient. Therefore, a need exits for an improved needle guide that will allow the placement of a needle into a target that is close to the surface of a patient.

SUMMARY OF THE INVENTION

The present invention is directed to a needle guide for controlling the direction of a needle as it enters a patient during imaging analysis and permitting a needle to be directed into a shallow target. The needle guide typically includes a curved path that permits a needle to enter into the needle guide at a first angle and then exit the needle guide at a different second angle near the surface of a patient. Typically the needle can enter the needle guide at an angle more obtuse to the surface of the patient than where it exits the needle guide. In this manner insertion of a needle into a patient is facilitated because the needle guide allows shallow needle placements, including needle placements that enter the skin at an angle approaching or parallel to the skin surface.

Needle guides made in accordance with the present invention generally include a channel for guiding the needle. This channel includes an inlet that is configured such that a needle inserted into it will form a first angle with the surface of a patient. The channel also has an outlet configured and arranged such that a needle will form a second angle with the surface of a patient. The second angle formed with the patient is typically less than the first angle. Typically the needle guide is constructed such that the needle has an exit angle of less than 30 degrees, more typically less than 20 degrees, and frequently less than 10 degrees. Also, often the exit angle made with a patient's surface is less than half the angle at the inlet to the channel.

Generally the angle of the needle changes because it travels down a curved path while within the needle guide. In most implementations the needle path is curved such that the needle has an angular change of at least 10 degrees over the length of the path; while in other implementations the angular change is greater than 20 degrees over the length of the path. Thus, a needle that enters the needle guide at an angle perpendicular to the patient will exit the needle guide at an angle of less than 80 degrees or 70 degrees, respectively, in these two implementations. In certain other implementations this difference in angles is at least 30 degrees, while in yet other implementations it is at least 45 or 60 degrees. In some implementations the difference in angles significantly exceeds 75 degrees and can approach or exceed 90 degrees. Thus, a needle guide that imparts a change of at least 60 degrees in the needle can have a needle enter the needle guide at an angle of 90 degrees to the patient, but exit the needle guide at an angle of 30 degrees or less relative to the patient.

In general it is desirable to have the needle make a significant bend while it travels through the needle guide, but then return to a substantially straight course upon exiting the needle guide. Typically the outlet and inlet portions of the path are coplanar and nonlinear. However, other non-coplanar implementations may also be used. In certain implementations the needle path also comprises an integrally formed canula that aids in the travel of the needle down the channel. Furthermore, in certain implementations the needle guide contains a second needle path, and optionally multiple needle paths. Also, in some implementations the needle remains rotatable within the guide even when within the channel. Other aspects of the invention are also directed to improvements that aid in removal of the needle from the needle guide without disturbing the placement of the needle within a patient.

The needle guide of the invention can be, for example, fully disposable, partially disposable, fully reusable, integrated with an imaging instrument, or secondary to the imaging instrument. Thus, in some implantations part or all of the needle guide is disposed after use, while in other implementations part or all of the needle guide is reused.

The above summary of the present invention is not intended to describe each discussed embodiment of the present invention. This is the purpose of the figures and the detailed description that follow.

BRIEF DESCRIPTION OF THE DRAWINGS

Other aspects and advantages of the invention will become apparent upon reading the following detailed description and references to the drawings, in which.

While the invention is susceptible to various modifications and alternative forms, specifics thereof have been shown by way of example and drawings, and will be described in detail. It should be understood, however, that the intention is not to limit the invention to particular described embodiments. On the contrary, the intention is to cover modifications, equivalents, and alternatives falling within the spirit and scope of the invention as defined by the appended claims.

DETAILED DESCRIPTION

The present invention is directed to a needle guide for use with an imaging instrument. The needle guide controls the direction of a needle as it enters a patient during imaging analysis, and in particular helps in controlling the angle at which the needle enters a patient. The invention allows a needle to enter a patient at a relatively acute angle, thereby permitting placement of the needle into a relatively shallow target that is near the surface of a patient, such as near the patient's skin or near the exterior of an organ being examined. These organs can include, for example, a breast, thyroid, vein, artery, skin, or other tissue.

The needle guide typically includes a curved path that permits a needle to enter the guide at a first angle and then exit the guide at a second angle relative to the surface of a patient. Typically the needle can enter the needle guide at an angle more obtuse to the surface of the patient than when it exits the needle guide. In this manner insertion of a needle into a patient is facilitated because the needle guide allows shallow needle placements which can enter the skin at an angle approaching parallel to the skin surface.

Figure 1A:
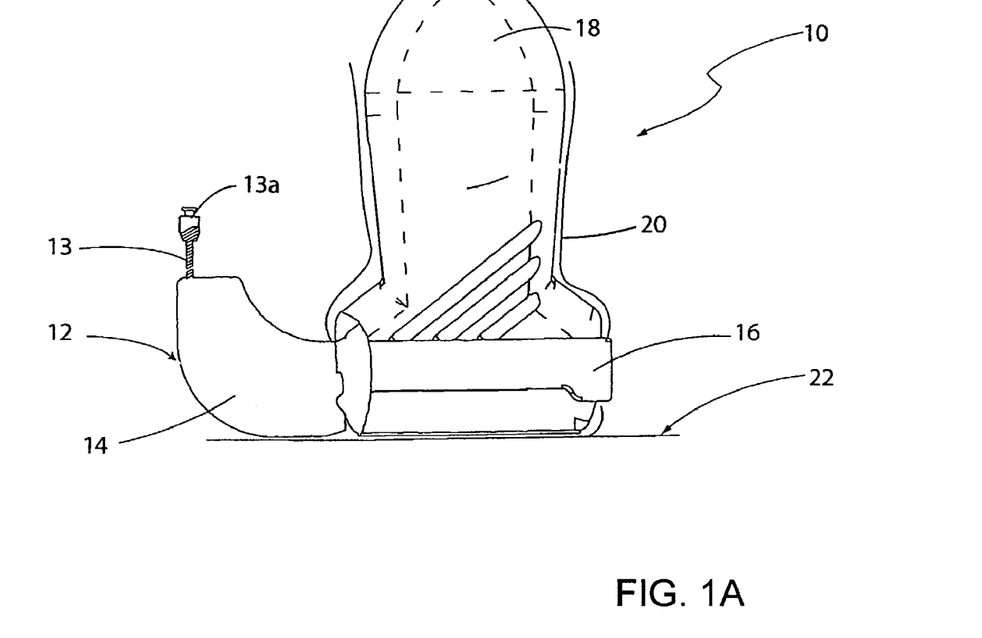
FIG. 1A is a side elevational view of needle guide constructed and arranged in accordance with an embodiment of the invention, showing the needle guide attached to an imaging probe.
Figure 1B:
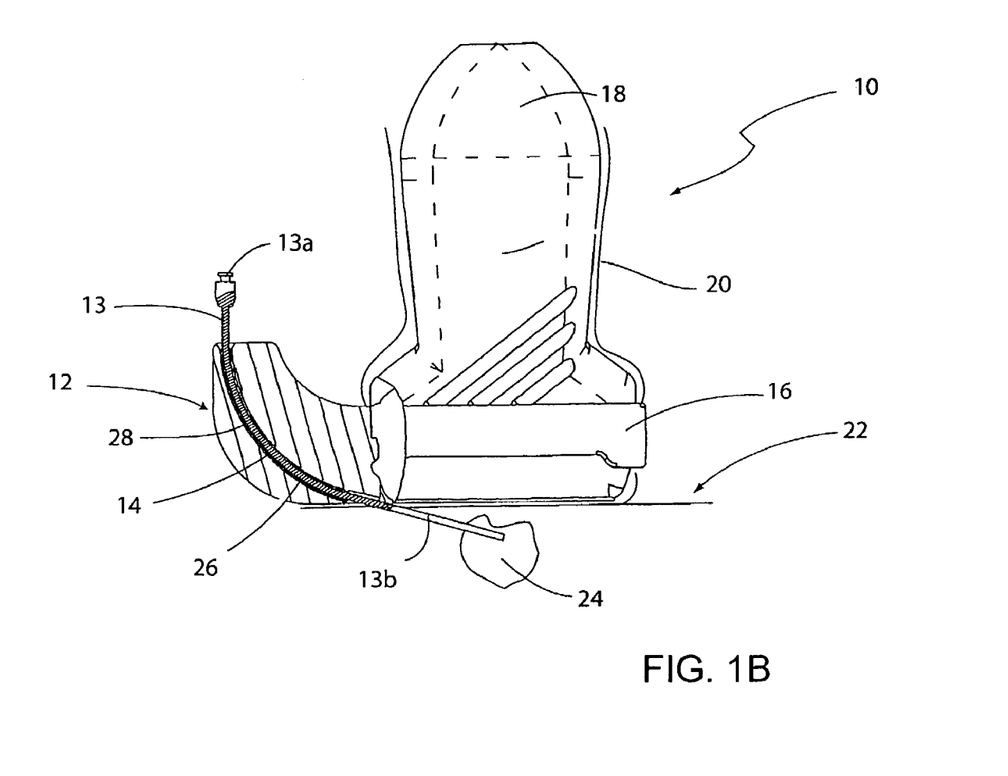
FIG. 1B is a side elevational view of the needle guide of FIG. 1A, showing the needle guide in partial cross section.

Referring now to the drawings, more aspects of the invention will be described. FIGS. 1A and 1B show a system 10 for guiding a needle 13 into a patient. System 10 includes needle guide 12, which has a guide portion 14 and a bracket portion 16. FIG. 1A shows the system 10 on a patient, while FIG. 1B shows the same view but with portions of the needle guide 12 and patient in cross section. The bracket 16 secures the needle guide 12 to an imaging probe 18. In the embodiment shown, the imaging probe 18 is an ultrasound probe, but it will be appreciated that other types of imaging and diagnostic instruments may also be used.

A sterile cover 20 is also shown in the embodiment of FIGS. 1A and 1B, and it covers the imaging probe 18. Typically such sterile covers 20 are made of a non-porous material that keeps the probe 18 free of contamination. In the depicted embodiment, the sterile cover 20 is placed over imaging probe 18 and then bracket 16 is placed over the cover 20. However, other configurations are also possible.

In addition, some implementations have the needle guide 12 integrally formed with the imaging probe 18, or secured by a means other than a bracket to the imaging probe 18. Thus, it is not necessary that a specific bracket be used, but merely that the guide portion 14 of the needle guide 12 perform in the manner described herein, and in particular that guide portion 14 allow a needle to be guided to a shallow target 24 beneath probe 18 (as shown in FIG. 1B).

Needle 13 is shown placed within guide portion 14 of needle guide 12. It will be observed that needle 13 has two ends 13a and 13b, and that needle 13 is bent within needle guide 12 such that the front end 13b enters a patient at a more acute angle to the surface 22 of a patient than the back end 13b of needle 13. In this manner needle 13 bends significantly and it enters a target 24 of a patient that is very close to the surface 22 of the patient.

FIG. 1B shows the same system 10 as depicted in FIG. 1A, but part of the guide portion 14 of needle guide 12 is depicted in cross section in order to reveal the needle path along channel 26 that gently curves to alter the exit angle of the needle 13 relative to the entrance angle. In addition, a canula 28 is placed within channel 26 and helps bend the needle 13. Canula 28 can be integrally formed with the rest of needle guide 12, or can be molded in place or otherwise positioned in channel 26. Suitable materials for canula 28 include metals (such as SST or aluminum, for example), plastic, nylon, glass, ceramic, fibers, etc. The purpose of canula 28 is to aid in the movement of the needle 13 within channel 26, and in particular to prevent the needle 13 from getting caught in the channel 26.

Figure 2A:
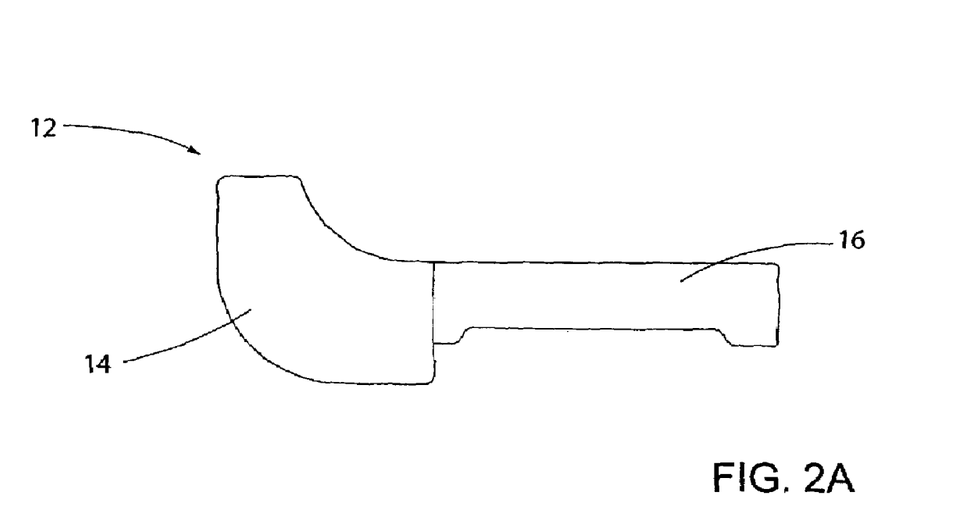
FIG. 2A is a side elevational view of a needle guide constructed and arranged in accordance with an embodiment of the invention, showing the needle guide without an imaging probe.
Figure 2B:
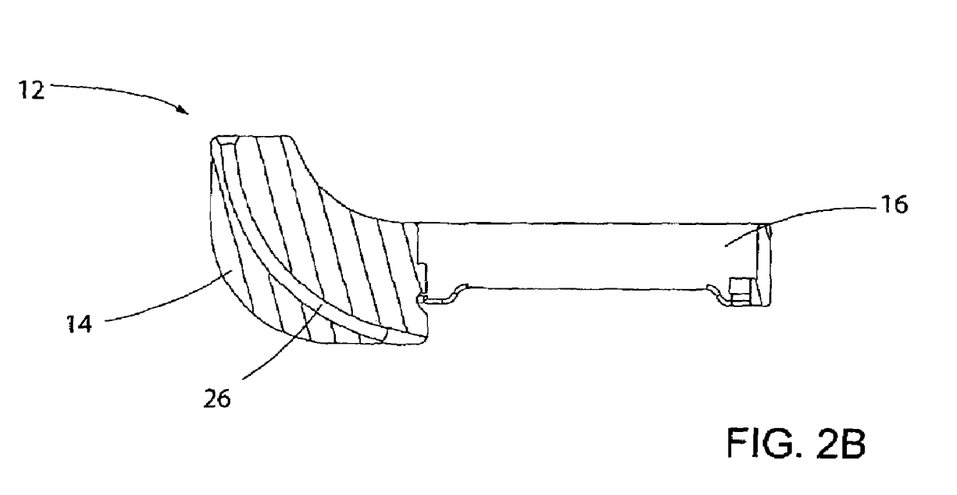
FIG. 2B is a side elevational view of the needle guide of FIG. 2A, showing the needle guide in cross section.

The elements of the needle guide 12 are also depicted in FIGS. 2A and 2B, but are shown without the imaging probe 18. Needle guide 12 includes guide portion 14 and bracket portion 16. The interior of needle guide 12 is revealed by the partial cross section of FIG. 2B. In this example embodiment a single channel 26 is positioned within guide portion 14 of needle guide 12. As noted below, this channel 26 can have various configurations, and indeed multiple channels can be present in guide portion 14. However, in all implementations the needle (not shown) is bent, curved, or reoriented within the needle guide 12 such that it has a different exit angle out the guide 12 (and into a patient) than its entrance angle into the guide 12.

Figure 3A:
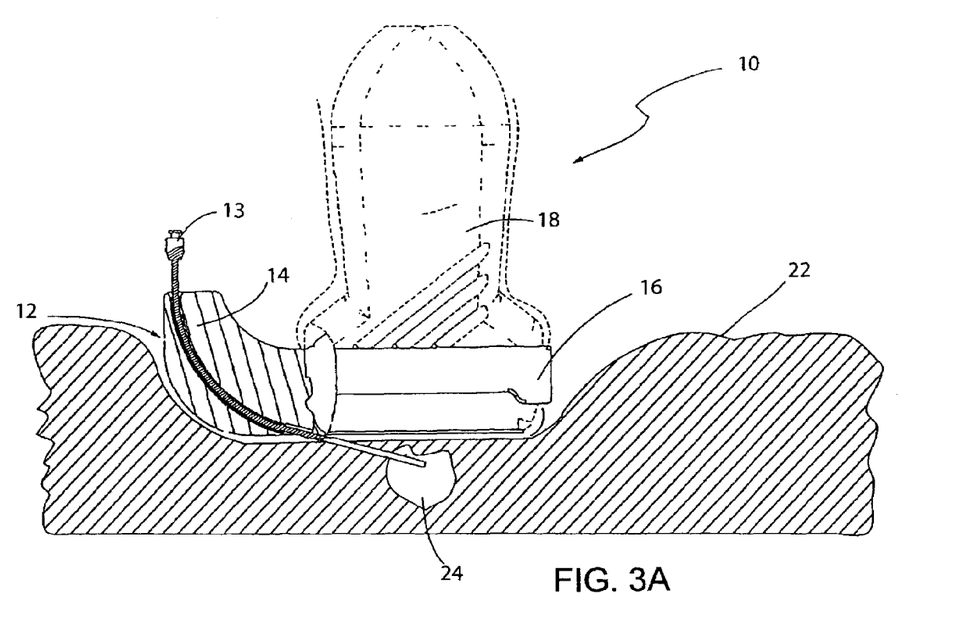
FIG. 3A is a partial cross sectional view of a needle guide constructed in accordance with an embodiment of the invention and installed on an ultrasound probe positioned on a curved surface of a patient.
Figure 3B:
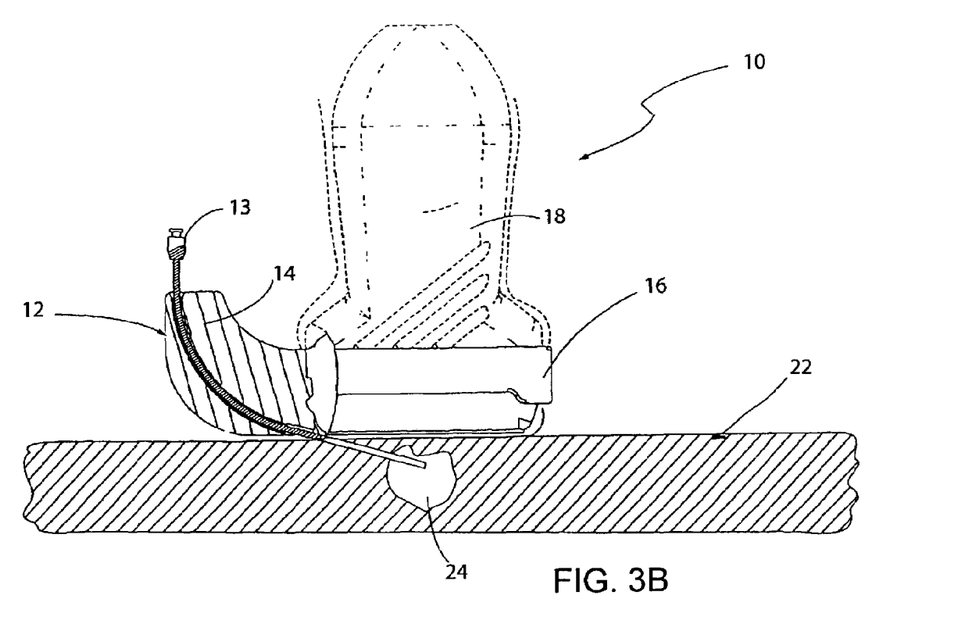
FIG. 3B is a partial cross sectional view of a needle guide constructed in accordance with an embodiment of the invention and installed on an ultrasound probe positioned on a flat surface of a patient.

Benefits of the present invention are readily identifiable in FIGS. 3A and 3B, which show that the present invention is particularly well suited to be used for placing a needle 13 within a target near the surface of a patient's skin, regardless of surface topography of the patient. In FIG. 3A the patient's surface has a great deal of relief and partially surrounds the imaging probe, including partially encompassing the guide portion 14 of the needle guide 12. An example where this situation can arise is in breast tissue or adipose deposits that create a soft, pliable substrate for the probe 18 (shown in phantom lines). Despite tissue partially surrounding the probe, it is possible to deliver a needle 13 near the surface 22 of the patient. Had the needle 13 not changed direction within needle guide 12 it would have not been possible to readily hit target 24 because the surrounding tissue is rising up around the needle guide 12, obscuring any straight-line access to target 24. FIG. 3B shows that the needle guide of the invention is also suitable for use on relatively flat surfaces 22 of a patient. Thus, the invention can be used on curved and flat surfaces of a patient.

One important aspect of the present invention is that the needle typically changes its direction while passing through needle guide 14. This aspect is clarified in FIG. 4, which shows how the entrance angle α and exit angle β are generally not the same, with exit angle β being smaller than entry angle α. Angle α is measured as the angle between the exposed shaft of needle 13 relative to a plane 15 parallel to the surface of the patient. In the event that imaging is being done trough an irregular surface, then the angle is generally measured relative to a plane 15 that is parallel to the surface of the patient beneath the probe (such as the area 23 of a patient's skin 22).

The amount of angular change or bend in the needle will vary in different implementations of the invention, but is generally controlled such as to enhance the ease of use and the accuracy of needle placement. Due to the fact that the needle must be bent during use, it is normally possible to have a greater angular change in thin needles as opposed to thick needles.

In some implementations the needle path is curved such that the needle path (the difference in degrees between α and β) has an angular change of at least 10 degrees over the length of the path; while in other implementations the angular change is greater than 20 degrees. Thus, a needle 13 that enters the needle guide 12 at an angle perpendicular to the patient will exit the needle guide at an angle of less than 80 degrees or less than 70 degrees, respectively, in these two implementations. In certain embodiments this difference in angles is at least 30 degrees, while in yet other implementations it is at least 45 or 60 degrees. In some implementations the difference in angles significantly exceeds 75 degrees and can approach or exceed 90 degrees. Thus, a needle guide that imparts a change of at least 60 degrees in the needle can have a needle enter at an angle of 90 degrees to the patient but exit the needle guide at 30 degrees or less relative to the patient.

In general it is desirable to have the needle make a significant bend while it travels through the needle guide, but then return to, a substantially straight form upon exiting the needle guide. Typically, the outlet and inlet portions of the channel are coplanar and nonlinear such that the needle bends within the channel but stays within one plane. However, it should be appreciated that certain implementations of the invention do not require a coplanar outlet and inlet. In such implementations the channel generally forms multiple turns or a complex turn that takes the inlet and outlet out of the same plane. Such implementations can be suitable for applications that have offset inlets or outlets that do not align with one another.

The needle guide can also contain a second needle path, and optionally multiple needle paths. For example, it is possible in certain implementations of the invention to have more than one path so that the needle direction can be adjusted depending upon the target location. This is particularly useful for implementations wherein the exact depth of the target is not known until after initiation of the imaging analysis. Using such multipath needle guides allows a user to utilize one needle guide to probe multiple target depths depending upon target location.

Alternatively, it is possible to incorporate an additional needle guide that attaches to the primary shallow angle needle guide. Thus, a needle guide configured for deeper penetration of a patient can be physically combined with the shallow angle needle guide in order to give greater flexibility in placement of a needle. Also, the shallow angle needle guide can be removable from a base or bracket so that it is interchangeable with other needle guides, or can be configured such that it is removably attached to other needle guides.

Figure 5A:
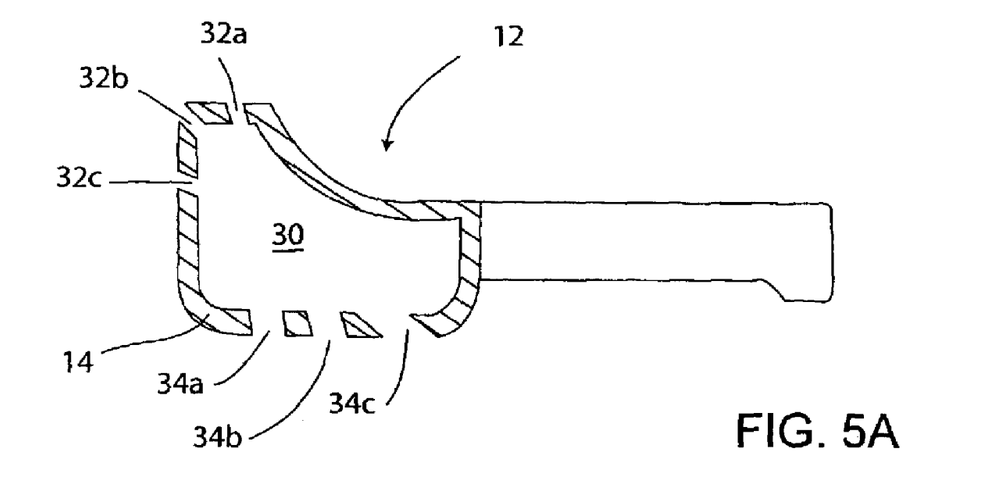
FIG. 5A is cross sectional view of a portion of a needle guide constructed and arranged in accordance with an implementation of the invention, the needle guide configured for insertion of needles at multiple angles.
Figure 5B:
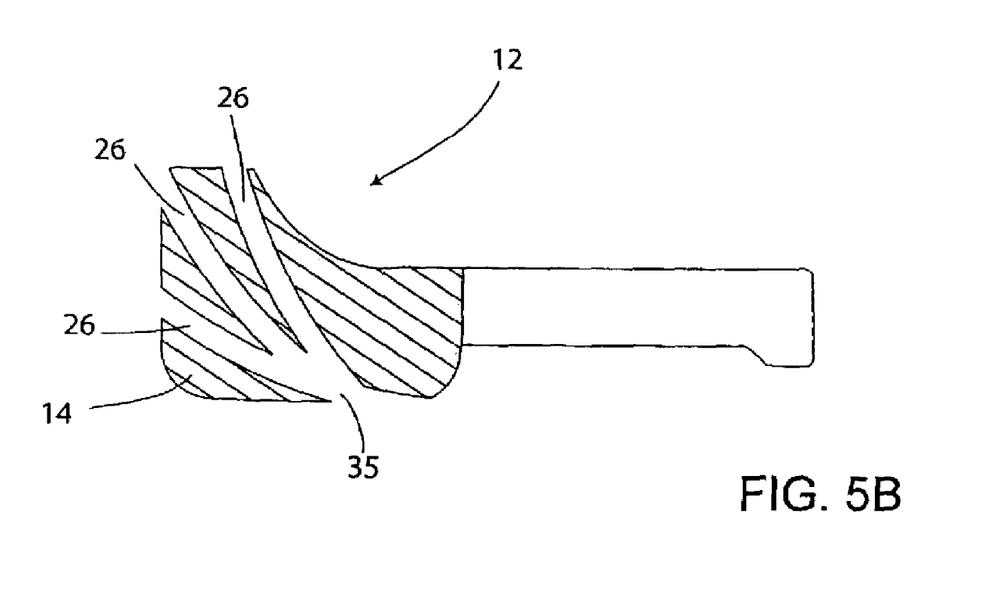
FIG. 5B is cross sectional view of a portion of a needle guide constructed and arranged in accordance with an implementation of the invention, the needle guide configured for insertion of needles at multiple angles.

Various options are available for creating multi-path needle guides. For example, FIG. 5A shows a central cavity 30 having multiple entrances and exits that combine to form multiple needle paths. Thus, entrance 32a and exit 34a combine to form one path, while entrance 32b and exit 32c forms a second path, and entrance 32c and exit 34c forms yet another path. In some such implementations there are multiple entrances and only one exit, or as shown here there can be multiple entrances and exits. The embodiment shown in FIG. 5A also indicates an implementation that has both shallow needle paths (32c to 34c) as well as deeper needle paths (such as 32a to 34a) An alternative multipath design is depicted in FIG. 5B, with multiple paths within the needle guide, which also permit different exit angles. In FIG. 5B each needle path is distinct but they come together near the exit 35. In this regard the needle paths 26 enter a patient's surface at the same location but with different trajectories.

Figure 4:
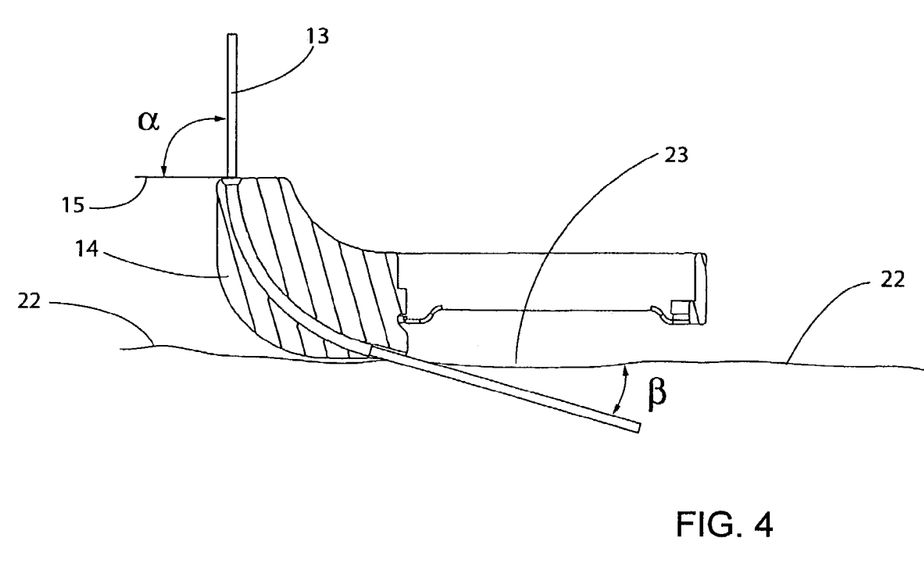
FIG. 4 is a side elevational view of a needle guide, further depicting the angles of the needle at the entrance and exit to the guide.
Figure 6A:
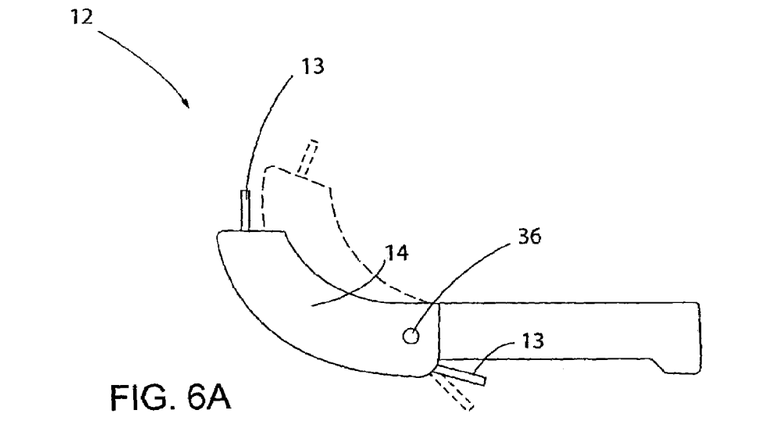
FIG. 6A is a side plan view of a needle guide having a pivoting portion.

An alternative way of adjusting the exit angle is shown in FIG. 6A, which depicts the guide portion 14 of needle guide 12 with a pivot point 36. Guide portion 14 is shown in solid lines in a first orientation and in dotted lines in a second orientation. Depending upon the angle at which the guide portion is adjusted, the orientation of the needle when it enters a patient can be significantly changed. However, the orientation is still typically relatively shallow (having a small β angle, as indicated in FIG. 4).

Figure 6B:
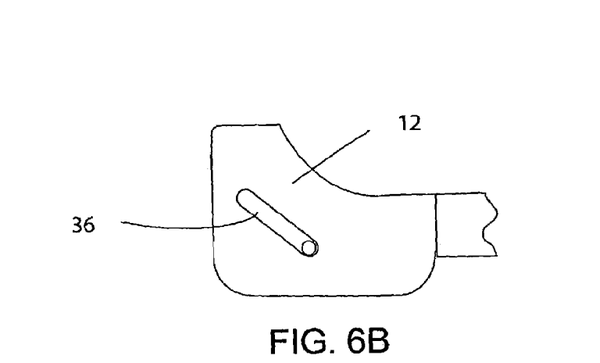
FIG. 6B is a side plan view of the needle guide having a pivoting channel of FIG. 6A.
Figure 6C:
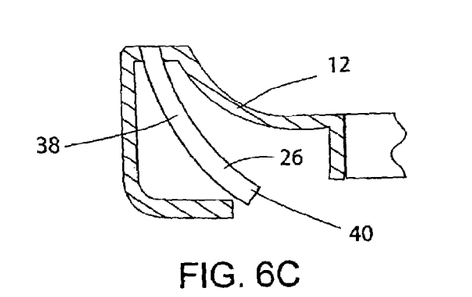
FIG. 6C is a side cross sectional view of the needle guide having a pivoting channel of FIG. 6B, the channel in a first position.
Figure 6D:
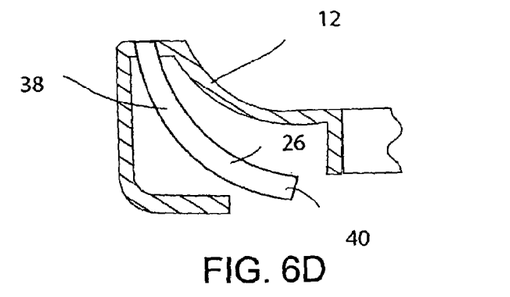
FIG. 6D is a side cross sectional view of the needle guide having a pivoting channel of FIG. 6B, the channel in a second position.

FIGS. 6B, 6C, and 6D show yet another implementation in which the channel moves or pivots. In most such implementations the channel is made of a flexible material, controlled by a lever 36 to adjust the position of tube 38 forming channel 26, thereby changing the angle at exit 40 of the channel.

Figure 7A:
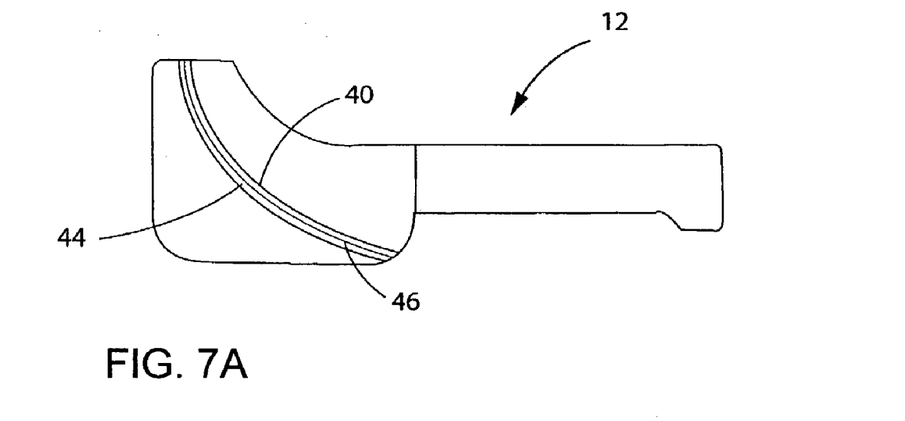
FIG. 7A is a side plan view of a portion of a needle guide constructed and arranged in accordance with an implementation of the invention showing a channel configured and arranged for the easy removal of a needle
Figure 7B:
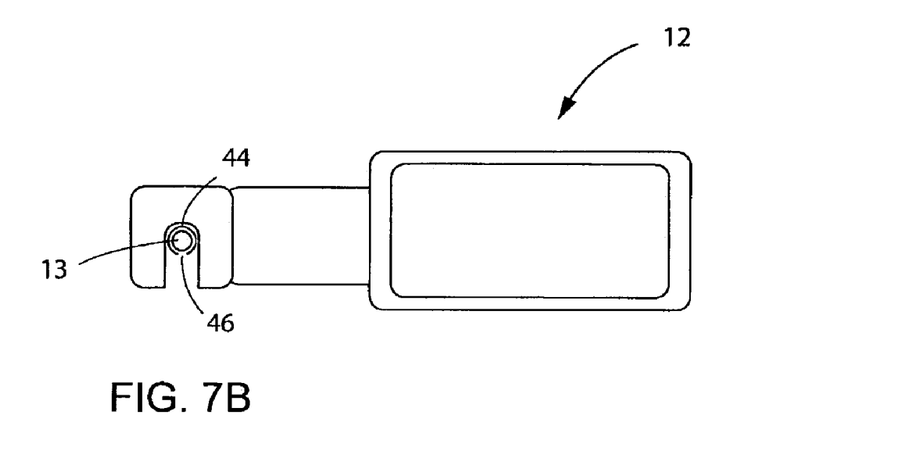
FIG. 7B is a top plan view of a portion of the needle guide of FIG. 7A, showing the needle within the needle guide.
Figure 7C:
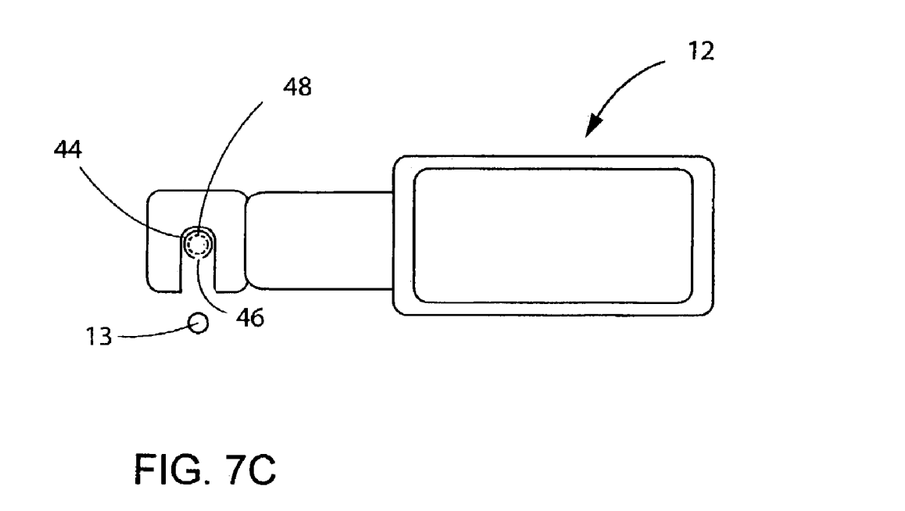
FIG. 7C is a top plan view of a portion of the needle guide of FIG. 7A, showing the needle removed from the needle guide.

In some implementations of the invention the needle can be easily removed from the needle guide without removing the needle from the patient. Example implementations of such embodiments are shown in FIGS. 7A to 7C and 8A to 8C. FIG. 7A shows a side elevational view of a needle guide 12, along with partial top views of the needle guide in FIGS. 7B and 7C. FIG. 7A shows an exposed channel 40 placed on a side of the needle guide 12. Channel 40 contains a pliable retainer 44 into which a needle is placed (depicted in greater detail in FIG. 7B). Pliable retainer 44 has a gap or cut 46 along its exposed edge, and this gap or cut 46 allows a needle 13 to be slipped out of the side of the needle guide 12 without removal of the needle 13 from a patient. This aspect of removing the needle 13 is better understood by looking at FIG. 7C, which shows the needle 13 outside of the pliable retainer 44, along with phantom dotted lines 48 of where the needle used to be within pliable retainer 44. Yet another implementation uses a snap-in tube to make a channel, the tube typically having multiple positions into which it can be snapped to have different angles for the inlet and outlet.

Pliable retainer 44 is generally a material that readily guides a needle but is sufficiently flexible to allow removal of the needle from channel 40. Suitable materials include flexible rubber or plastic hoses or tubes. The pliable retainer 44 can be snapped into place, glued with an adhesive, or otherwise secured in a manner that allows removal along the gap or cut.

Figure 8A:
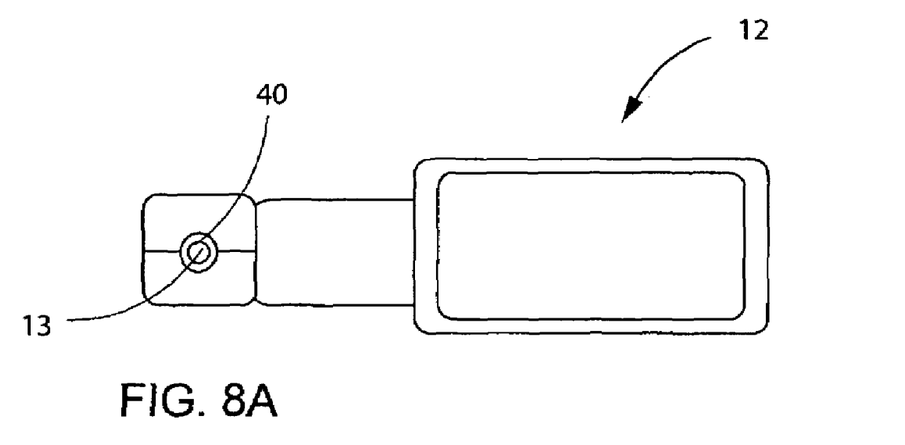
FIG. 8A is a top plan view of the needle guide showing a needle within the needle guide.
Figure 8B:
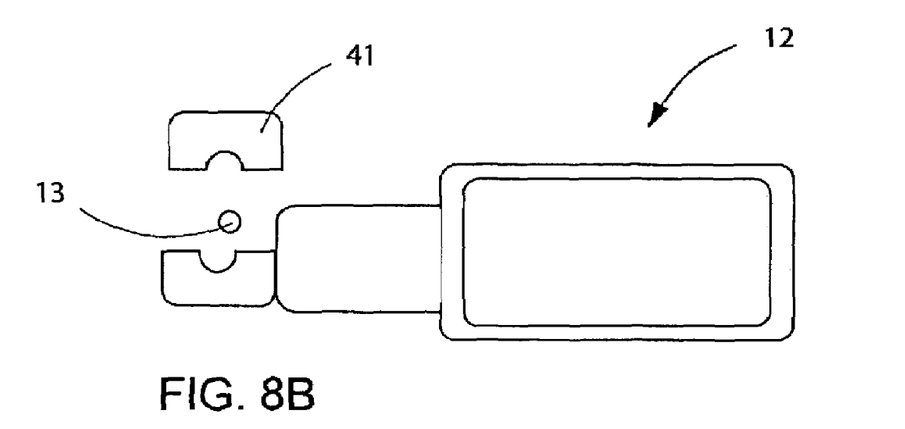
FIG. 8B is a top plan view of the needle guide of FIG. 8A, showing the needle removed from the needle guide.
Figure 8C:
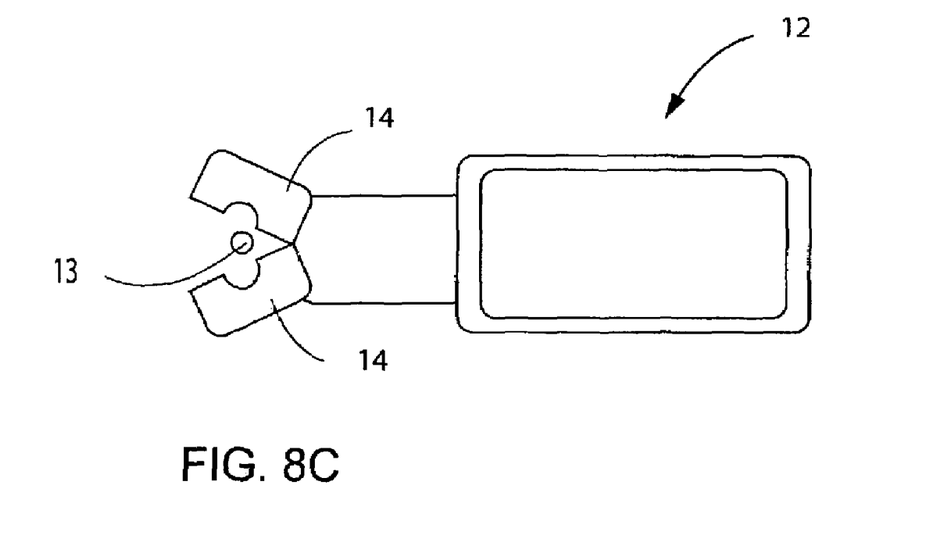
FIG. 8C is a top plan view of the needle guide of FIG. 8A, showing the needle removed from the needle guide.

Additional methods of removing a needle from the needle guide are shown in FIGS. 8A to 8C, which are top plan views of needle guides made in accordance with the invention. FIG. 8A shows a closed needle guide 12 containing a needle 13 in channel 40, while FIG. 8B shows removal of the needle after lifting away an exterior door 41 or wall that holds the needle 13 in place within channel 40. Alternatively, the needle 13 can be removed by having a two-part guide portion 14 that is hinged to open and release the needle. 13 from the channel 40, as shown in FIG. 8C

As described above, the needle guide can also include an elastic sheath that covers a portion of the imaging instrument, thereby maintaining sterility. Suitable materials used for forming the elastic sheath include natural and synthetic latex rubber, as well as various elastomers suitable for contact with a patient. The elastomers are preferably hypoallergenic. Although the elastic sheath is ideally disposed after use on each patient, it is alternatively sterilized between uses so that it can be used on more than one patient. In certain embodiments, the cover is used to conduct imaging analysis on multiple patients, and is therefore constructed of a material suitable for sterilization, such as various plastic compositions. However, in alternative embodiments the cover-is used for only one medical procedure and is disposed after each use.

It will be appreciated that although the implementation of the invention described above is directed to an ultrasound probe, the present device may be used with other medical imaging modalities, and is not limited to ultrasound probes. In addition, while the present invention has been described with reference to several particular implementations, those skilled in the art will recognize that many changes may be made hereto without departing from the spirit and scope of the present invention.

We claim:

1. A needle guide system for delivering a needle during imaging analysis, the needle guide system comprising:
    a needle path defined between an entrance for the needle into a needle guide and an exit for a front end of the needle out of the needle guide and into outer surface of a patient, the needle path comprising a curved portion configured and dimensioned for bending the needle between the entrance and the exit;
    an ultrasound probe configured to be placed proximate the outer surface of a patient;
    wherein the exit is disposed proximate an edge of the ultrasound probe that in part defines a region of imaging; and
    wherein the needle guide is coupled to the ultrasound probe.

2. The needle guide system of claim 1, wherein the needle path is curved such that the needle path has an angular change of at least 10 degrees over the length of the path.

3. The needle guide system of claim 1, wherein the needle path is curved such that the needle path has an angular change of at least 20 degrees over the length of the path.

4. The needle guide system of claim 1, wherein the needle path is curved such that the needle path has an angular change of at least 30 degrees over the length of the path.

5. The needle guide system of claim 1, wherein the needle path is curved such that the needle path has an angular change of at least 45 degrees over the length of the path.

6. The needle guide system of claim 1, wherein the needle path is curved such that the needle path has an angular change of at least 60 degrees over the length of the path.

7. The needle guide system of claim 1, wherein the needle path is curved such that the needle path has an angular change of from about 45 to 90 degrees over the length of the path.

8. The needle guide system of claim 1, wherein outlet and inlet portions of the path are coplanar and nonlinear.

9. The needle guide system of claim 1, wherein the path comprises an integrally formed canula.

10. The needle guide system of claim 1, further comprising a second path, the second path substantially coplanar with the needle path.

11. The needle guide system of claim 10, wherein the second path has an exit angle different than an exit angle of the needle path.

12. The needle guide system of claim 1, wherein the needle guide further comprises a pliable channel permitting removal of the needle along the length of the channel.

13. A needle guide system for delivering a needle during imaging analysis, the needle guide system comprising:
    a needle guide comprising:
        a curved channel configured for receiving a needle;
        the channel having an inlet portion, an outlet portion, and a needle path therebetween, wherein the needle path proximate the inlet portion is disposed at an angle with respect to the needle path proximate the outlet portion;
    an ultrasound probe configured to be placed proximate skin of a patient;
    wherein the outlet portion is disposed proximate an edge of the ultrasound probe that in part defines a region of imaging; and
    wherein the needle guide system is configured such that the system remains outside of a patient during imaging analysis.

14. The needle guide system of claim 13, wherein the outlet and inlet portions of the channel are coplanar.

15. The needle guide system of claim 13, wherein the channel comprises an integrally formed canula.

16. The needle guide system of claim 13, wherein the inlet portion is configured and arranged such that the needle inserted therein is disposed at a first angle and the outlet portion is configured and arranged such that the needle inserted therein is disposed at a second angle, the second angle being less than the first angle.

17. The needle guide system of claim 13, wherein the outlet portion has an exit angle that is less than 10 degrees.

18. The needle guide system of claim 13, wherein the inlet portion has an entrance angle and the outlet portion has an exit angle, the exit angle being less than half the entrance angle.

19. The needle guide system of claim 13, wherein the inlet portion has an entrance angle and the outlet portion has an exit angle, the entrance angle being substantially perpendicular to a surface of the patient for needle penetration and the exit angle being substantially parallel to the surface of the patient for needle penetration.

20. The needle guide system of claim 13, wherein the needle guide further comprises a pliable portion permitting removal of the needle along the length of the channel.

21. A shallow angle needle guide system configured and arranged for guiding a needle into outer surface of a patient undergoing imaging analysis, the needle guide system comprising:
a needle guide comprising:
an inlet, the inlet configured and arranged such that the needle partially placed within the needle guide will form an angle of at least 30 degrees with the outer surface of the patient;
an outlet, the outlet configured and arranged such that a portion of the needle exiting the needle guide will form an angle of less than 30 degrees with the outer surface of the patient;
an ultrasound probe configured to be placed proximate the outer surface of the patient;
wherein the outlet is disposed proximate an edge of the ultrasound probe that in part defines a region of imaging; and
wherein the needle guide system is configured such that the system remains outside of the patient during imaging analysis.

22. The shallow angle needle guide system of claim 21, wherein the inlet and outlet have an angular difference with respect to the outer surface of the patient of at least 10 degrees.

23. The shallow angle needle guide system of claim 21, wherein the needle is permitted to rotate within the guide.

24. The shallow angle needle guide system of claim 21, wherein the needle guide further comprises a channel between the inlet and outlet.

25. The shallow angle needle guide system of claim 24, wherein at least part of the channel can be opened to permit removal of the needle from the needle guide.

26. The shallow angle needle guide system of claim 21, wherein the needle guide comprises multiple paths that come together at the outlet.

27. A system for directing a needle comprising:
an ultrasound probe configured to be placed adjacent skin of at patient;
a sterile cover configured and dimensioned to separate surfaces of the ultrasound probe from direct contact with the skin of the patient;
a needle guide coupled to the ultrasound probe and fixed in position with respect thereto, the needle guide comprising a curved portion configured to receive and guide a needle out an exit of the needle guide and toward a region of imaging by the ultrasound probe;
wherein the exit is disposed proximate an edge of the ultrasound probe that in part defines the region of imaging.

28. The system of claim 27, wherein the curved portion comprises a plurality of curved channels.

29. The system of claim 27, wherein the curved portion comprises a channel selectively positionable within the needle guide.

30. The system of claim 27, wherein the needle guide is demountably coupled to the ultrasound probe.

31. The system of claim 27, wherein the needle guide further comprises a bracket portion demountably coupled to the ultrasound probe.

32. The system of claim 27, wherein the curved portion comprises at least two discrete, curved needle paths.

33. The system of claim 32, wherein each of the needle paths terminates proximate the same location at the exit.

34. The system of claim 27, wherein the curved portion comprises a plurality of needle entrances.

35. The system of claim 27, wherein the curved portion is movable.

36. The system of claim 27, wherein the curved portion is rotatable.

37. The system of claim 27, wherein the curved portion comprises a plurality of paths defined between a plurality of separate entrances to the needle guide and the exit.

38. A method of directing a needle in a percutaneous procedure comprising:
placing an ultrasound probe adjacent skin of a patient proximate a location for performing the procedure through the skin;
coupling a needle guide to the ultrasound probe in a fixed position with respect thereto, the needle guide comprising a curved portion;
guiding a needle within the curved portion of the needle guide and out an exit of the needle guide so that the needle is oriented toward a region of imaging by the ultrasound probe.

39. The method of claim 38, further comprising:
extending the needle to a target beneath the skin of the patient.

40. The method of claim 39, wherein the target is disposed near the skin of the patient.

41. The method of claim 39, wherein the exit is disposed proximate an edge of the ultrasound probe that in part defines the region of imaging.

42. The method of claim 38, wherein the needle guide comprises a bracket portion and the needle guide is coupled to the ultrasound probe by demountably attaching the bracket portion to the ultrasound probe.

43. The method of claim 38, wherein the curved portion comprises at least two discrete, curved needle paths and the method further comprises selecting one of said paths for guiding said needle.

44. The method of claim 43, wherein each of the needle paths terminate proximate the same location at the exit.

45. The method of claim 38, wherein the curved portion comprises a plurality of needle entrances and the method further comprises selecting one of said entrances for initially guiding said needle in said needle guide.

46. The method of claim 38, wherein the curved portion is movable and the method further comprises selecting an orientation of the curved portion by moving the curved portion.

47. The method of claim 38, wherein the method further comprises moving the curved portion to select an angle for the needle to exit the needle guide with respect to the skin.

48. The method of claim 38, further comprising:
rotating the curved portion.

49. A method of directing a needle in a percutaneous procedure comprising:
placing an ultrasound probe adjacent skin of a patient proximate a location for performing the procedure through the skin;
coupling a needle guide to the ultrasound probe in a fixed position with respect thereto, the needle guide comprising a plurality of curved paths definable between a plurality of separate entrances to the needle guide and at least one exit to the needle guide;
selecting one of the curved paths;
guiding a needle within the selected curved path so that the needle penetrates the skin while oriented toward a region of imaging by the ultrasound probe.

50. The method of claim 49, wherein the needle guide is demountably coupled to the ultrasound probe.

51. The method of claim 49, wherein the needle guide comprises a single exit for the needle, with each of the curved paths leading to the single exit.

52. The method of claim 49, wherein the curved paths are integrally formed in the needle guide between the entrances and the at least one exit.

53. The method of claim 49, wherein the needle guide comprises a single exit for the needle, with the exit disposed proximate an edge of the ultrasound probe that in part defines the region of imaging.

* * * * *